US006403793B2

(12) United States Patent
Pye et al.

(10) Patent No.: US 6,403,793 B2
(45) Date of Patent: Jun. 11, 2002

(54) INTRAMOLECULAR GLYCOSIDATION PROCESS FOR THE SYNTHESIS OF (2R, 2-ALPHA-R, 3A)-2-[1-(3,5- BIS (TRIFLUOROMETHYL) PHENYL)ETHOXY]-3-(4-FLUOROPHENYL)-1,4-OXAZINE

(75) Inventors: Philip J. Pye, Guttenberg, NJ (US); Kai Rossen, Degussa Huls AG (DE)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/877,883

(22) Filed: Jun. 8, 2001

Related U.S. Application Data
(60) Provisional application No. 60/211,015, filed on Jun. 12, 2000.

(51) Int. Cl.[7] .............................................. C07D 265/32
(52) U.S. Cl. ........................ 544/170; 544/106; 544/177
(58) Field of Search ................................ 544/170, 106, 544/177

(56) References Cited

U.S. PATENT DOCUMENTS 5,719,147 A * 2/1998 Dorn et al. ............... 514/227.5
5,877,316 A * 3/1999 Haworth et al. ............ 544/138
5,968,934 A * 10/1999 Swain et al. ............. 514/230.4

OTHER PUBLICATIONS

*Reference were mailed with prior office Action mailed on Aug. 24, 2001.*

* cited by examiner

*Primary Examiner*—Floyd D. Higel
*Assistant Examiner*—Kamal Saeed
(74) *Attorney, Agent, or Firm*—J. Eric Thies; Melvin Winokur

(57) ABSTRACT

The present invention is concerned with novel processes for the preparation of (2R-cis)-2-[[1-[3.5-bis(trifluoromethyl) phenyl]ethenyl]oxy]-3-(4-fluorophenyl)-4-(phenylmethyl) mopholine. This compound is useful as an intermediate in the synthesis of compounds which possess pharmacological activity.

8 Claims, No Drawings

INTRAMOLECULAR GLYCOSIDATION PROCESS FOR THE SYNTHESIS OF (2R, 2-ALPHA-R, 3A)-2-[1-(3,5- BIS (TRIFLUOROMETHYL) PHENYL)ETHOXY]-3-(4-FLUOROPHENYL)-1,4-OXAZINE

CROSS REFERENCE TO RELATED APPLICATIONS

This application claims the benefit of Provisional Application No. 60/211,015, filed Jun. 12, 2000.

BACKGROUND OF THE INVENTION

The present invention relates to processes for the preparation of (2R, 2-alpha-R, 3a)-2-[1-[3,5-bis(trifluoromethyl)phenyl]ethoxy-3-(4-fluorophenyl)-1,4-oxazine which is useful as an intermediate in the preparation of certain therapeutic agents. In particular, the present invention provides a process for the preparation of (2R, 2-alpha-R, 3a)-2-[1-[3,5-bis(trifluoromethyl)phenyl]ethoxy-3-(4-fluorophenyl)-1,4-oxazine which is an intermediate in the synthesis of pharmaceutical compounds which are substance P (neurokinin-1) receptor antagonists.

The general processes disclosed in the art for the preparation of (2R, 2-alpha-R)-4-benzyl-2-[1-[3,5-bis(trifluoromethyl)phenyl]ethoxy-1,4-oxazin-3-one result in relatively low and inconsistent yields of the desired product (see U.S. Pat. No. 5,719,147). In contrast to the previously known processes, the present invention provides more practical and economical methodology for the preparation of (2R, 2-alpha-R, 3a)-2-[1-[3,5-bis(trifluoromethyl)phenyl]-ethoxy-3-(4-fluorophenyl)-1,4-oxazine in relatively high yield and purity.

It will be appreciated that (2R, 2-alpha-R, 3a)-2-[1-[3,5-bis(trifluoro-methyl) phenyl]ethoxy-3-(4-fluorophenyl)-1,4-oxazine is an important intermediate for a particularly useful class of therapeutic agents. As such, there is a need for the development of a process for the preparation of (2R, 2-alpha-R, 3a)-2-[1-[3,5-bis (trifluoromethyl)phenyl] ethoxy-3-(4-fluorophenyl)-1,4-oxazine which is readily amenable to scale-up, uses cost-effective and readily available reagents and which is therefore capable of practical application to large scale manufacture.

Accordingly, the subject invention provides a process for the preparation of (2R, 2-alpha-R, 3a)-2-[1-[3,5-bis (trifluoromethyl)phenyl]ethoxy-3-(4-fluorophenyl)-1,4-oxazine via a very simple, short, relatively inexpensive and highly efficient synthesis.

SUMMARY OF THE INVENTION

The novel process of this invention involves the synthesis of (2R, 2-alpha-R, 3a)-2-[1-[3,5-bis(trifluoromethyl)phenyl] ethoxy-3-(4-fluorophenyl)-1,4-oxazine. In particular, the present invention is concerned with novel processes for the preparation of a compound of the formula:

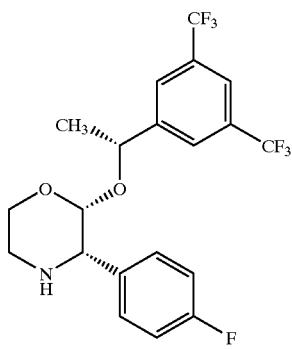

This compound is an intermediate in the synthesis of compounds which possess pharmacological activity. In particular, such compounds are substance P (neurokinin-1) receptor antagonists which are useful e.g., in the treatment of psychiatric disorders, inflammatory diseases, and emesis.

DETAILED DESCRIPTION OF THE INVENTION

The present invention is directed to processes for the preparation of (2R, 2-alpha-R, 3a)-2-[1-[3,5-bis (trifluoromethyl)phenyl]ethoxy-3-(4-fluorophenyl)-1,4-oxazine of the formula:

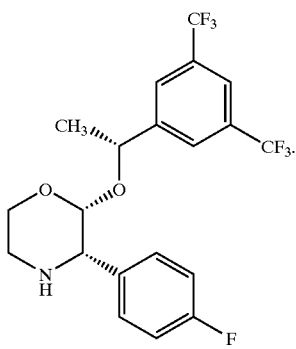

An embodiment of the general process for the preparation of (2R, 2-alpha-R, 3a)-2-[1-[3,5-bis(trifluoromethyl)phenyl] ethoxy-3-(4-fluorophenyl)-1,4-oxazine of the formula:

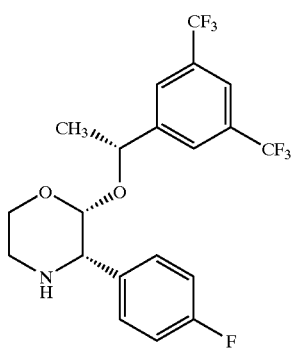

comprises:

(1) contacting a compound of the formula:

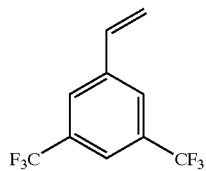

with an oxidizing agent to give a compound of the formula:

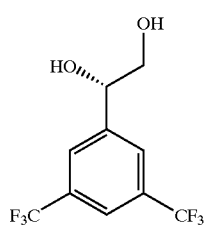

(2) activating such compound with an activating agent and contacting the activated compound with ethanolamine to give a compound of the formula:

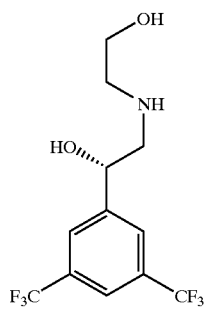

(3) condensing such compound with glyoxal and 4-fluoroboronic acid to give a compound of the formula:

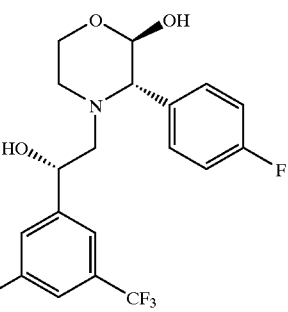

(4) intramolecular coupling of such activated compound to give a compound of the formula:

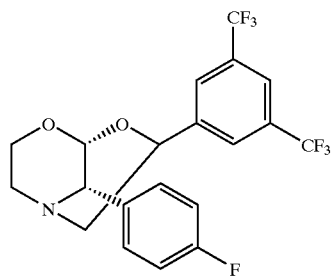

(5) quarternizing the amino group of such compound to give a compound of the formula:

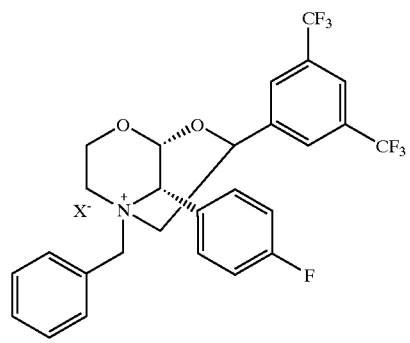

(wherein $X^-$ is a counterion)

(6) hydrolysis of such compound to give a compound of the formula:

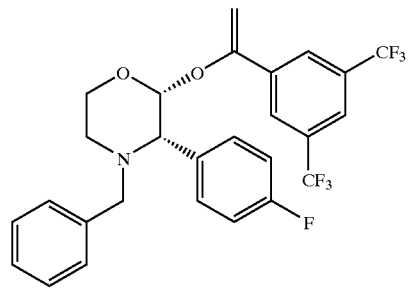

and (7) hydrogenation of such compound to give the compound of the formula:

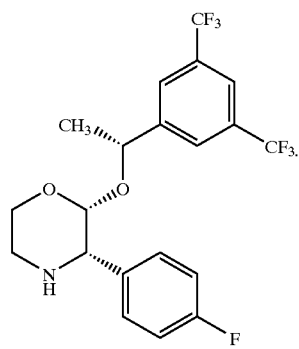

A specific embodiment of the process for the preparation of (2R, 2-alpha-R, 3 a)-2-[1-[3,5-bis(trifluoromethyl)phenyl]ethoxy-3-(4-fluorophenyl)-1,4-oxazine of the formula:

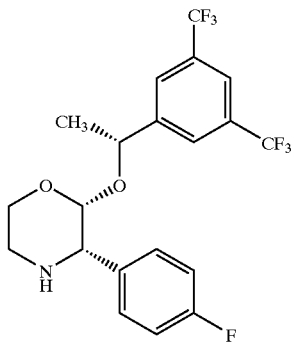

comprises:

(1) contacting a compound of the formula:

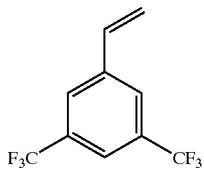

with an oxidizing agent selected from osmium tetroxide/N-methyl morpholine to give a compound of the formula:

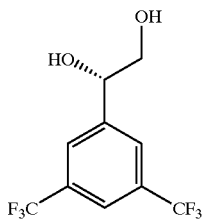

(2) activating such compound with an activating agent selected from methanesulfonyl chloride and contacting the activated compound with ethanolamine to give a compound of the formula:

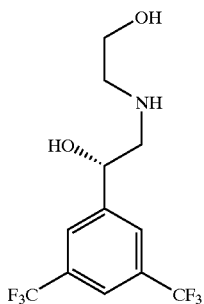

(3) condensing such compound with glyoxal and 4-fluoroboronic acid to give a compound of the formula:

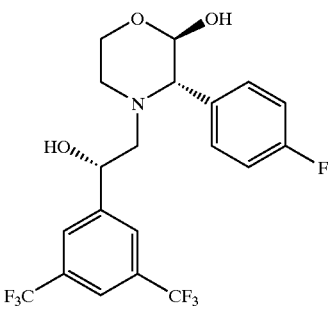

(4) intramolecular coupling of such activated compound under Mitsunobu conditions to give a compound of the formula:

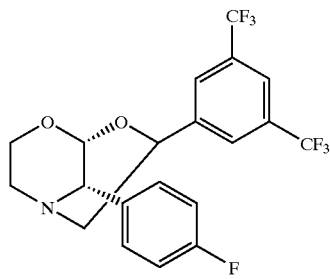

(5) quarternizing the amino group of such compound with a benzyl halide to give a compound of the formula:

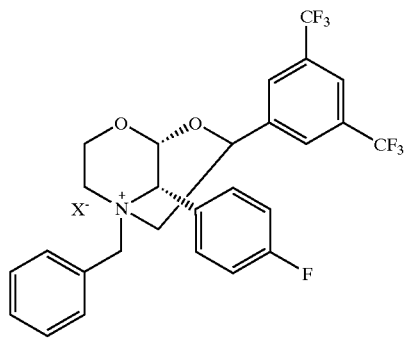

(wherein $X^-$ is a counterion)

(6) hydrolysis of such compound with an inorganic base to give a compound of the formula:

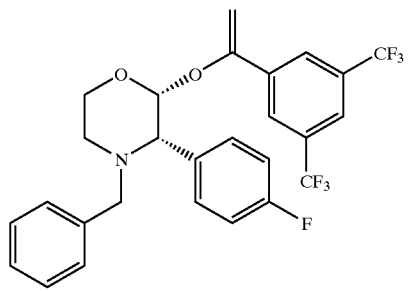

and (7) catalytic hydrogenation of such compound with a palladium catalyst to give the compound of the formula:

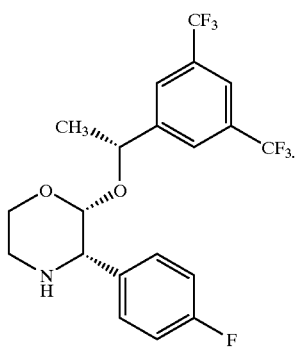

Another embodiment of the present invention concerns a process for the preparation of a compound of the formula:

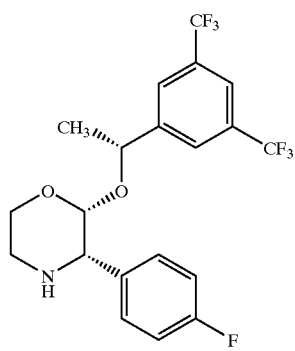

which comprises hydrogenation of a compound of the formula:

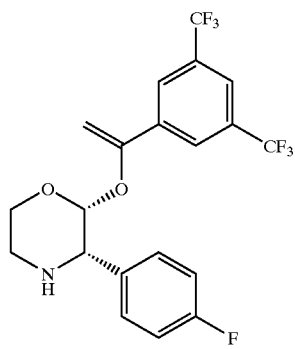

to give the compound of the formula:

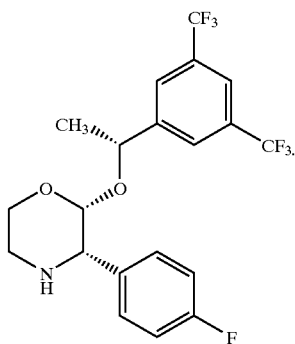

In this embodiment it is preferred that the hydrogenation is catalytic hydrogenation. It is preferred that the hydrogenation catalyst is a palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst). It is more preferred that the hydrogenation catalyst is palladium on carbon, especially 5% or 10% palladium on carbon. It is preferred that the solvent for the hydrogenation comprises a solvent which is selected from the group of $C_1$–$C_4$ primary, secondary and tertiary alcohols, and water. Preferred solvents for the hydrogenation comprise methanol, ethanol, isopropanol, n-propanol, n-butanol, water, and mixtures thereof. More preferred solvents for the hydrogenation comprise ethanol or methanol and mixtures thereof with water. It is preferred that the temperature of the reaction mixture for the hydrogenation is from about 10° C. to about 50° C., wherein the most preferred temperature is about 20–25° C. It is preferred that the pressure of hydrogen during the hydrogenation is from about 1 to about 150 psi, wherein the most preferred pressure is about 5 to about 50 psi.

Another embodiment of the process for the preparation of (2R, 2-alpha-R, 3a)-2-[1-[3,5-bis(trifluoromethyl)phenyl]ethoxy-3-(4-fluorophenyl)-1,4-5 oxazine of the formula:

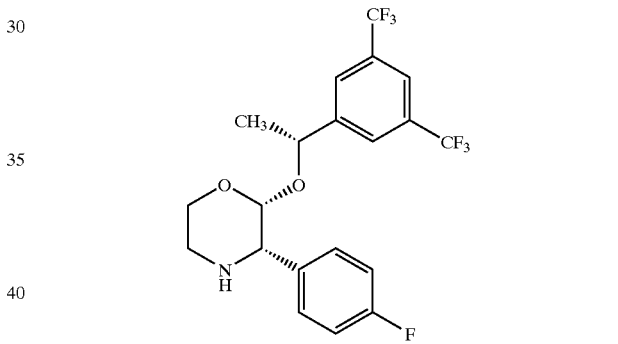

comprises the processes as outlined in the following Scheme.

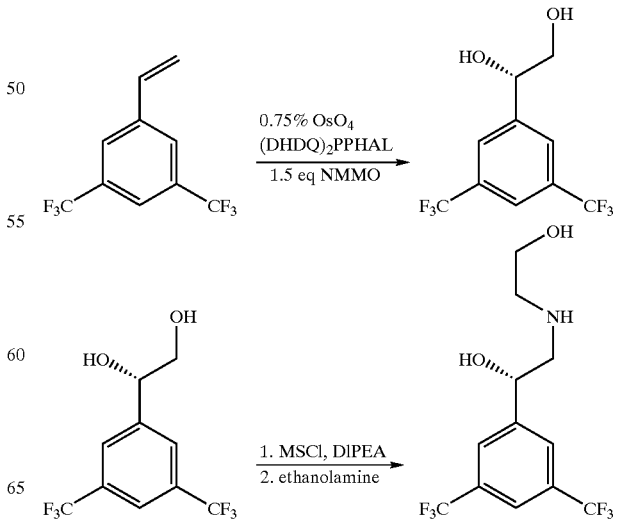

9
-continued
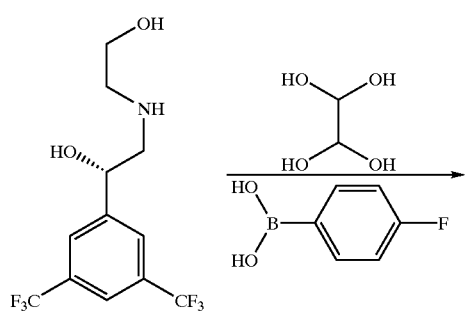
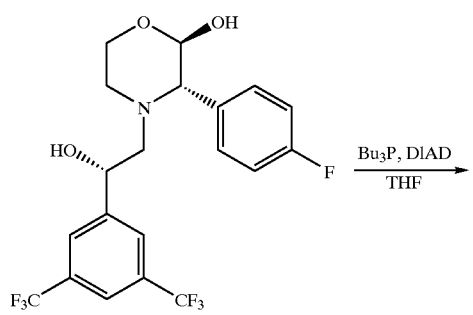
Bu₃P, DlAD
THF
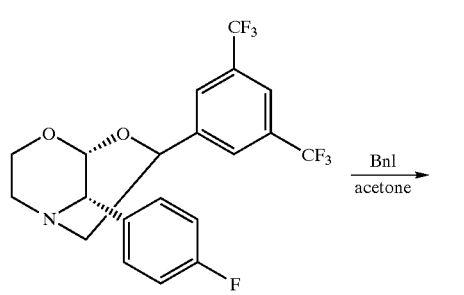
BnI
acetone
10
-continued
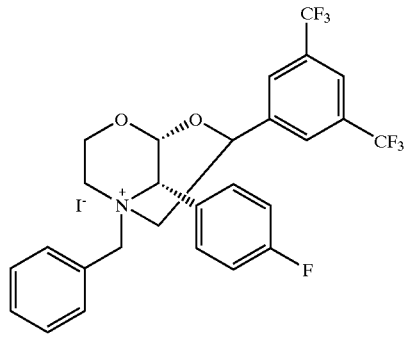
NaOH
EtOH/H₂O
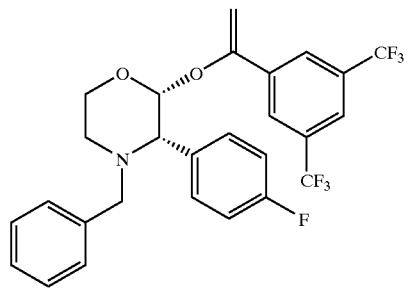
H₂, Pd/C
EtOH
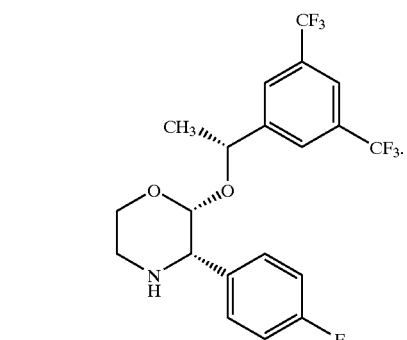

Another embodiment of the present invention is directed to the processes as outlined in the following Schemes.

As depicted in Scheme 1, a retrosynthetic analysis of 1 indicates a possible disconnection at the acetal center leading to 3,5-bis(trifluoromethyl)-sec-phenethyl alcohol 3 and the activated morpholine 2. Unfortunately, this glycosidation-type approach fails because either facile elimination of the leaving group (LG) or substitution from the β-face resulted in the undesired trans stereochemistry, presumably due to steric blocking by the adjacent 4-fluorophenyl group. Alternatively, vinyl ether 4 is a desirable intermediate because diastereoselective hydrogenation of the vinyl ether provides (2R-cis)-2-[[1-[3.5-bis (trifluoromethyl)phenyl]ethenyl]oxy]-3-(4-fluorophenyl)-4-(phenylmethyl)-mopholine (Hale, et al., *J. Med. Chem.* 1998, 41, 4607.) Importantly, 4 is retrosynthetically transformed to the bicyclic quaternary ammonium salt 5 by a regioselective Hofmann elimination. The critical cis-stereochemistry in 5 is set by an intramolecular displacement of the lactol hydroxyl group of 6, thus overcoming the bias towards the trans arrangement. Lactol 6 is derived from chiral aminodiol 7 using a Mannich boronic acid condensation. It was imperative to the success of this strategy that the single stereocenter of aminodiol 7 controls both stereocenters in the morpholine ring of 6.

Synthesis of aminodiol 7 in racemic or enantiomerically pure form is achieved using known chemistry. A Sharpless asymmetric dihydroxylation of 3,5-bis(trifluoromethyl) styrene (8) set up the necessary absolute stereochemistry and subsequent selective activation of the primary alcohol as the mesylate followed by displacement with ethanolamine lead cleanly to crystalline 7. A three-component condensation is then utilized to assemble the core morpholine ring system in one step from 7.

As depicted in Scheme 2, heating 7 with 4-fluorophenylboronic acid (9) and aqueous glyoxal affords a mixture of lactol diastereomers: 6, 10 and 11 (50:10:<2 area %) and regioisomers 12 and 13 (10 and 20 area %), respectively. A chromatographically isolated mixture of 10 and 11 returns to the initially observed isomeric mixture of 6, 10, 11, 12 and 13 by addition of DBU, cat. $H_3PO_4$ or by simple heating. This facile equilibration of the isomers in solution, coupled with a crystallization of the desired diastereomer, leads to a crystallization-induced transformation that funnels the complex mixture into a single crystalline isomer. This crystallization induced asymmetric transformation was first demonstrated in the racemic series by seeding the mixture of 6, 10, 11, 12 and 13 with crystalline rac-6 to afford the desired rac-6 in 65% yield (90 A %).

As depicted in Scheme 3, repeating the boronic acid condensation with (S)-7, provides the expected ratio of isomers in solution. However, attempts to crystallize enantiomerically-pure trans lactol 6 were unsuccessful and resulted in the isolation of a minor component of the reaction. mixture, the cis lactol 11. Pure 11 is obtained in 86% yield by slow crystallization of the reaction mixture from methylcyclohexane. Because the trans lactol 6 is the thermodynamically preferred species in solution, brief exposure of a solution of the cis lactol 11 to a trace amount of $H_3PO_4$ rapidly establishes a 87:13 equilibrium of trans:cis lactols 6 and 11.

The cis lactol 6 is converted to trans lactol 6 by equilibration of a solution of 11 to the 87:13 trans:cis mixture and slow precipitation of the trans lactol 6 as the HCI salt. A simple conversion to the free base gives a solution of clean trans lactol 6, which is stable at 20° C. for extended periods of time in the absence of strong bases or acids.

Although a number of the lactol isomers could potentially cyclize to bicyclic acetal 14, attempts to achieve this transformation under traditional acetal forming conditions resulted in complex mixtures. Treatment of a solution of 6 with tributylphosphine in THF at −30° C. followed by the addition of DIAD and warming to ambient temperature gives crystalline bicyclic acetal 14.

As depicted in Scheme 4, the bicyclic acetal is quaternized in acetone with benzyl iodide at 50° C. to yield 89% of salt 5. Regioselective Hofmann elimination proceeds by heating 5 in ethanol/water (3:1) with 1.1 equivalents of sodium hydroxide. The choice of iodide counterion for salt 5 allowed the direct isolation of the key vinyl ether intermediate 4 in 90% yield with rejection of the sodium iodide byproduct in the liquors.

SCHEME 1

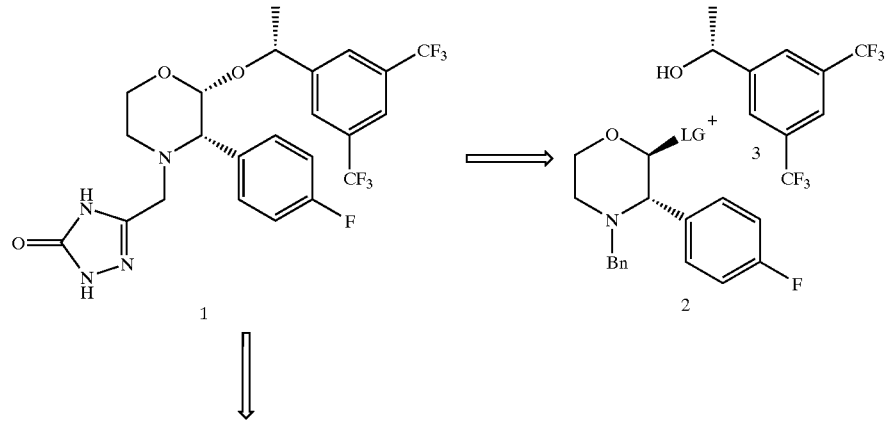

-continued
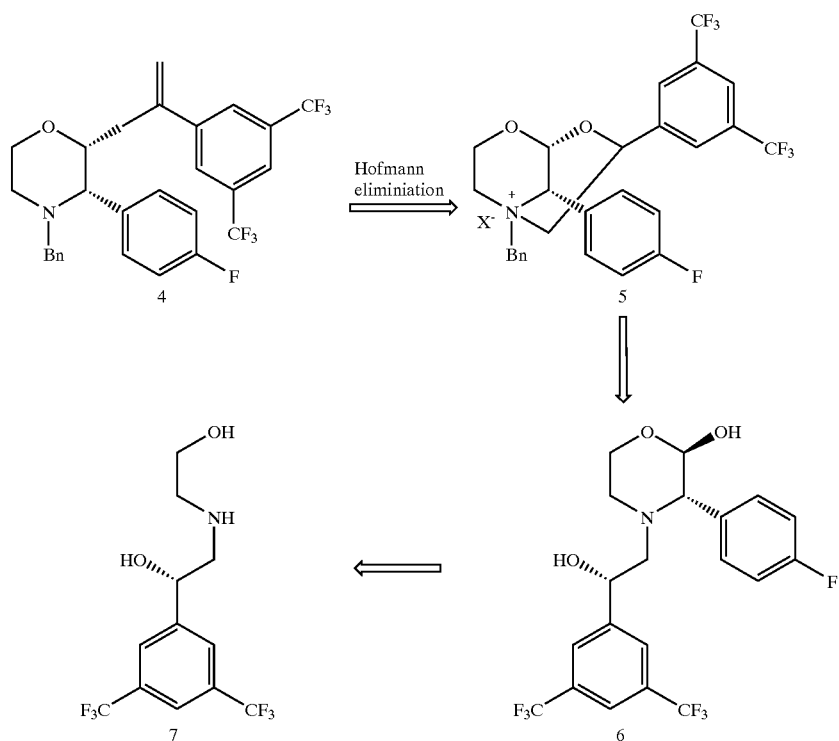
SCHEME 2
INTERCONVERSION OF DIASTEREOMERS
7 + 4-fluorophenylboronic acid (9) + aqueous glyoxal
↓ tert-amylalcohol
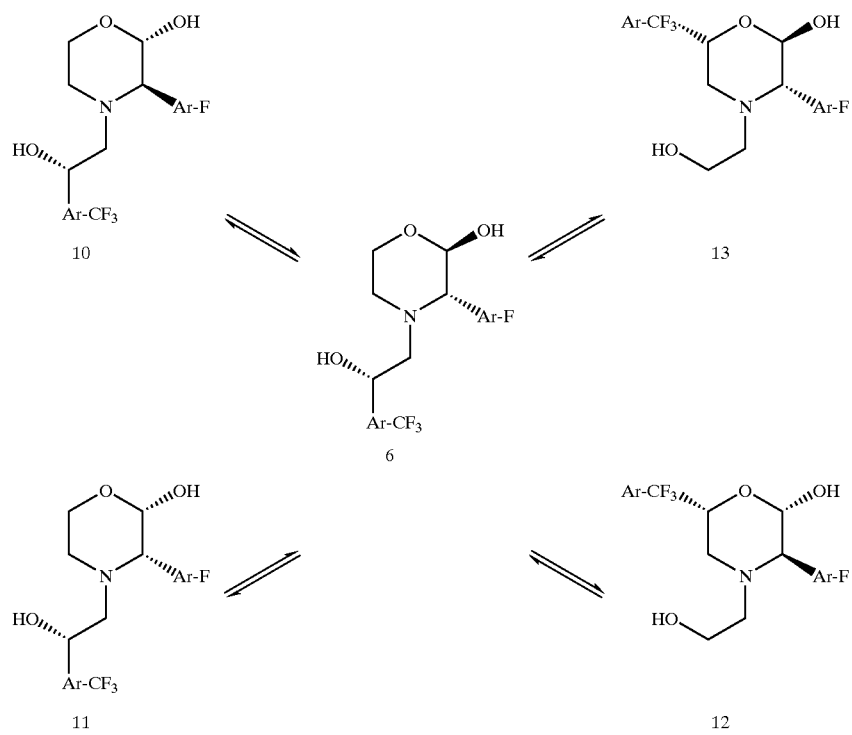

-continued
Ar-CF$_3$ = 3,5-bis(trifluoromethyl)phenyl   Ar-F = 4-fluorophenyl
SCHEME 3
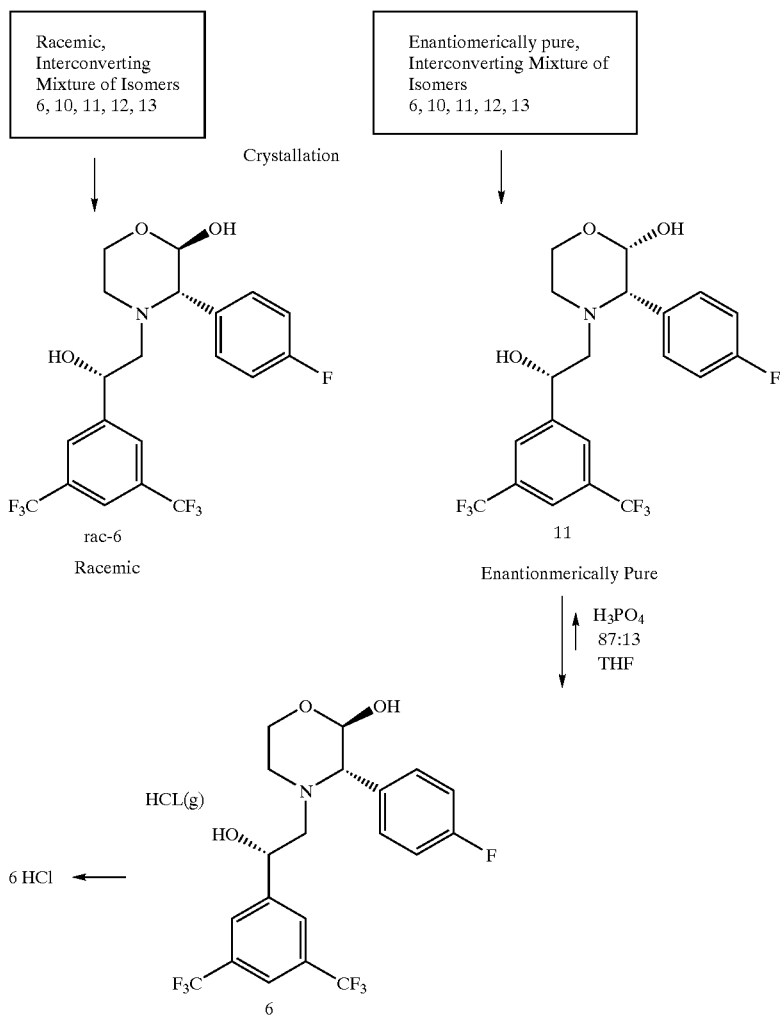
SCHEME 4
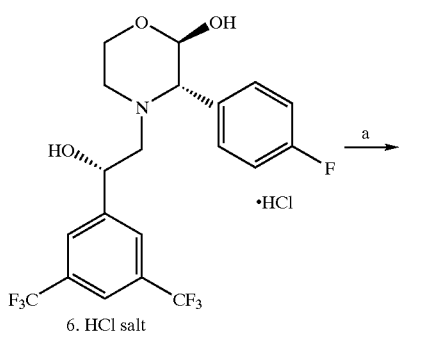
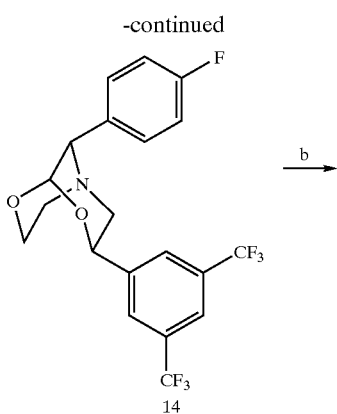

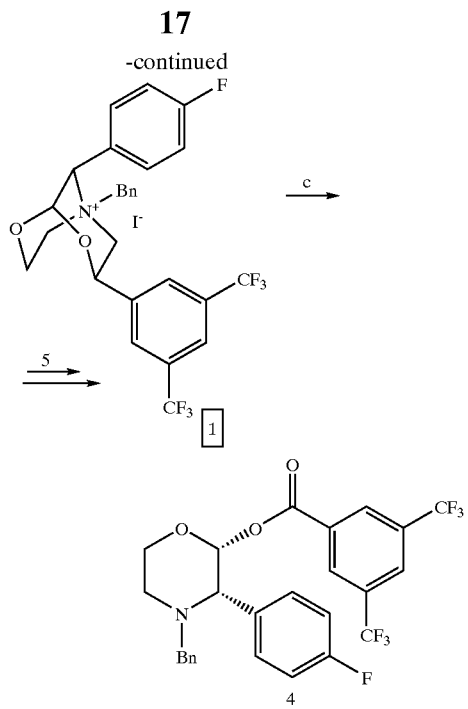

Reagents: (a)(i) aq. $K_2CO_3$, EtOAc (ii) $Bu_3P$, DIAD, THF, −30° C. to 20° C., 86%; (b) BnI, acetone, 50° C., 89%; and (c) 1.1 eq. NaOH, EtOH, $H_2O$, 90%.

The (2R, 2-alpha-R, 3a)-2-[1-[3,5-bis(trifluoromethyl)phenyl]ethoxy-3-(4-fluorophenyl)-1,4-oxazine obtained in accordance with the present invention may be used as starting material in further reactions directly or following purification.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

3,5-Bis(trifluoromethyl)bromobenzene

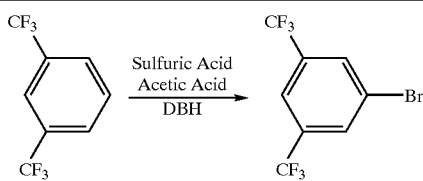

| Materials | MW | Density | Amount | Mmol | Equiv. |
|---|---|---|---|---|---|
| 1,3-Bis(trifluoromethyl)benzene | 214.1 | 1.38 | 107 g | 500 | 1.0 |
| 96% $H_2SO_4$ | | | 142 mL | | |
| Glacial HOAc | | | 22 mL | | |
| 1,3-Dibromo-5,5- | 285.93 | | 77.25 g | 270 | 1.08 |

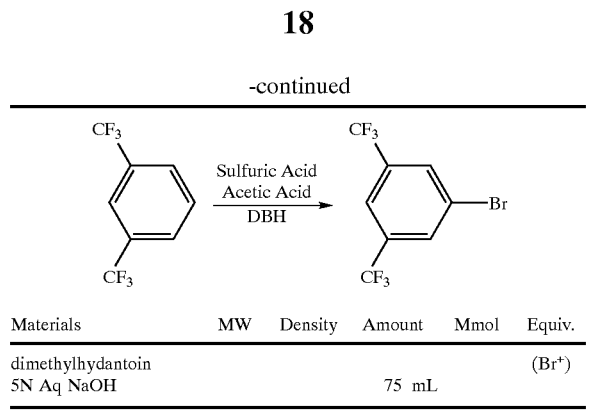

| Materials | MW | Density | Amount | Mmol | Equiv. |
|---|---|---|---|---|---|
| dimethylhydantoin | | | | | (Br⁺) |
| 5N Aq NaOH | | | 75 mL | | |

A vigorously stirred solution of 1,3-bis(trifluoromethyl)benzene (107 g) in a mixture of glacial acetic acid (22 mL) and concentrated sulfuric acid (142 mL) was added 1,3-dibromo-5,5-dimethylhydantoin (77.25g) at 25° C. The exothermic reaction raised the temperature to approximately 40° C. After aging at 45° C. for 4.5 h, the mixture was cooled to approximately 0° C. and poured into cold water (250 mL). After washing with 5N NaOH (75 mL) the organic layer contained 137 g of the desired 3,5-bis(trifluoromethyl)-1-bromobenzene by assay (94% yield). This product was used in the next step without further purification.

EXAMPLE 2

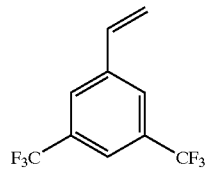

3,5-Bis(trifluoromethyl)styrene

A solution of 3,5-bis(trifluoromethyl)-1-bromobenzene (75 g, 0.256 mol), tetiabutylammonium chloride (71.4 g, 0.256 mol), triethylamine (71.3 mL, 0.97 mol) and palladium(II) acetate (113 mg) in acetonitrile (360 mL) was deoxygenated with a vigorous flow of nitrogen. The reaction was pressurized with ethylene (950 psi) and heated to 80° C. for 36 hours. Pentane (400 mL) was added and after 3 water washes (200 mL) the organic layer was dried over $Na_2SO_4$ and the solvent was removed in vacuo to afford 3,5-bis(trifluoromethyl)styrene as a pale yellow oil (58.2 g, 0.242 mol, 95% yield).

EXAMPLE 3

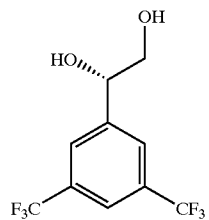

(S)-Bis-3,5-(trifluoromethyl)phenyl ethyleneglycol (DHQ)₂PHAL (13.3 g, 17.0 mmol) was added to a solution of potassium osmate dihydrate (5.68 g, 15.4 mmol) in tert-butanol (2.3 L) water (1.97 L). An aqueous solution of N-methylmorpholine N-oxide (596 mL, 50wt. %, 2.88 mol) was then added. After 15 minutes 468 g of 3,5-bis (trifluoromethyl)styrene (1.95 mol) was added over 3.5 hours maintaining a temperature of 15° C. The reaction mixture was warmed to 23° C. for 30 minutes and quenched by the addition of 10% aq. Na$_2$SO$_3$. After aging for 18 hours the phases were separated and the aqueous layers extracted with ethyl acetate (1×2 L). The organic layers were combined, washed with 0.4 N H$_2$SO$_4$ saturated with Na$_2$SO$_4$ (2.4 L). After drying over Na$_2$SO$_4$ the solvent was removed in vacuo to afford crude (S)-bis-3,5-(trifluoromethyl)phenyl ethyleneglycol as an off white solid (87% ee). Recrystallization from ethyl acetate/hexanes gave (S)-bis-3,5-(trifluoromethyl)phenyl ethyleneglycol as a white solid (395 g, 74%,>99% ee): ): mp 142–144° C.; $[\alpha]^{25}_{589}$ =19.85° (2.833, MeOH); $^1$H NMR. IR (KBr) 3312, 2896, 1622, 1473 cm$^{-1}$. Anal. Calcd for C$_{10}$H$_8$F$_6$O$_2$ C 43.81; H, 2.94; F, 41.58. Found: C, 43.45; H, 2.77; F,41.93.

EXAMPLE 4

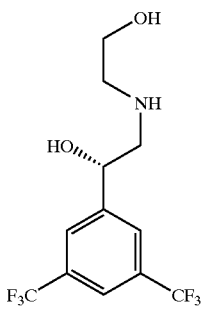

(S)-2-Imino[1-(bis-3,5-(trifluoromethyl)phenyl) ethanol]-2'-ethanol

Methanesulfonyl chloride (89 mL, 1.26 mol) was added over 1 hour to a solution of (S)-bis-3,5-(trifluoromethyl) phenyl ethyleneglycol (300 g, 1.09 mol) in acetonitrile (900 mL) containing 2,6-lutidine (600 mL, 5.2 mol). HPLC analysis indicated complete consumption of diol. After addition of 2-aminoethanol (1 L) the acetonitrile and 2,6-lutidine were removed by reduced pressure distillation at 90° C. over 3 hours. The remaining oil was partitioned between 10% aqueous sodium carbonate (1 L) and ethyl acetate (1.2 L). The organic layer was washed with water (3×300 mL) and then with brine (1×300 mL). After drying with MgSO$_4$ the solvent was removed to afford an oil. Crystallization from MBTE/heptane afforded 59% of (S)-2-imino[1-(bis-3, 5-(trifluoromethyl)phenyl)ethanol]-2'-ethanol as a white solid (205 g, 0.647 mol): mp 80–82° C.; $[\alpha]^{25}_{589}$ =34.4° (2.64, MeOH); $^1$H NMR. IR (KBr)2973, 2868, 1427, 1029 cm$^{-1}$. Anal. Calcd for C$_{12}$H$_{13}$F$_6$NO$_2$ C 45.43; H, 4.13; F, 35.93; N 4.42. Found: C, 45.15; H, 3.77; F, 35.89; N, 3.77.

EXAMPLE 5

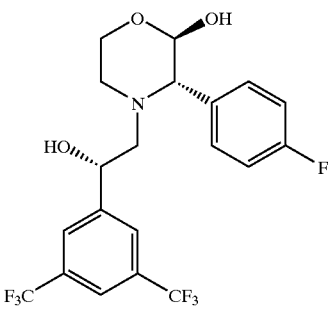

Lactol

To a solution of aminodiol (S)-2-imino[1-(bis-3,5-(trifluoromethyl)-phenyl)ethanol]-2'-ethanol (632 mg, 2.00 mmol) in 10 mL of tert-amylalcohol were added a 40% aqueous glyoxal solution (0.46 mL, 2 equiv.). After a 60 min age, 4-fluorophenylboronic acid (335 mg, 2.54 mmol) was added and the reaction mixture was heated to 40° C. for 15 hours. The reaction mixture was diluted with cyclohexane (80 mL) and washed with water (3×30 mL). Drying (MgSO$_4$) and evaporation gave a glassy solid, consisting of the diastereomeric mixture 13, 14, 15, 16 and 17 (1.06 g), which partially crystallized on standing. After addition of 4 mL of methylcyclohexane and 0.15 mL of EtOAc the resulting slurry is aged for 18 hours in a 45° C. bath to give the crystalline cis lactol 11 (775 mg, 95 A %, 86% yield): mp 130–132° C.; $[\alpha]^{25}_{589}$=; $^1$H NMR; IR (KBr) 3395, 1029, 800 cm$^{-1}$. Anal. Calcd for C$_{20}$H$_{18}$F$_7$NO$_3$: C 52.99; H, 4.00; F, 29.33; N 3.09. Found: C, 52.62; H, 3.91; F, 29.25;N, 3.03.

EXAMPLE 6

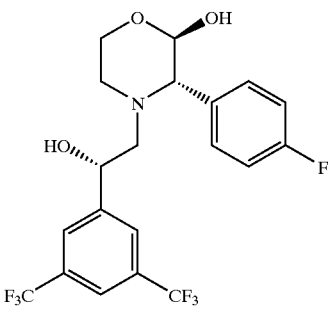

HCl salt (6)

A solution of the cis lactol 11 (705 mg, 1.57 mmol) in EtOAc (10 mL) is saturated with HCl gas. To the clear solution of the salt is added methylcyclohexane (10 mL). The slow crystallization is allowed to take place over 18 hours, when the slurry is concentrated to about half its volume and filtered to give the desired salt (747 mg, 94 A %, 98% yield). ): mp 176–178° C.; $[\alpha]^{25}_{589}$ =77° (c=4.7, MeOH); $^1$H NMR ; IR (KBr) 3278, 3059, 1098, 959 cm$^{-1}$. Anal. Calcd for C$_{20}$H$_9$ClF$_7$NO$_3$: C 49.04; H, 3.91; Cl, 7.24; F, 27.15; N, 2.86. Found: C, 48.65; H, 3.77; Cl, 7.36; F, 26.9; N, 2.81.

EXAMPLE 7

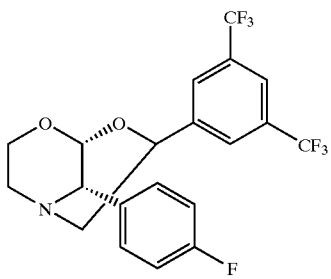

Bicyclic Acetal (14)

A slurry of lactol HCl salt (6) (4.25 g, 8.68 mmol) in ethyl acetate (50 mL) was washed with dilute aqueous potassium carbonate (0.7 g in 70 mL). The organic layer was further washed with water and dried over MgSO$_4$. The solvent was switched into THF (40 mL) and the solution cooled to −30° C. Tributylphosphine (2.65 mL, 10.4 mmol) was added followed by a the addition of DIAD (2.0 mL, 9.98 mmol) over 30 minutes maintaining a temperature below −25° C. After the addition the reaction was allowed to warm to 15° C. over 3 hours and the solvent was removed in vacuo. The residue was filtered through a short silica gel column (20% ethylacetate in hexane) and recrystallized from EtOH/water (1:1) to afford the bicyclic acetal as a white solid (3.23 g, 7.43 mmol, 86% yield): mp 99–101° C.; $[\alpha]^{25}_{589}$=23.5° (c=1.36,MeOH); $^1$H NMR; IR (KBr) 3073, 2976, 1016,935 cm$^{-1}$.

EXAMPLE 8

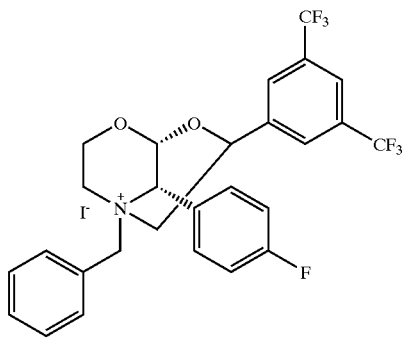

Bicyclic Acetal Quaternary Ammonium Iodide (5)

Benzyl chloride (0.7 mL; 6.08 mmol) was added to a solution of sodium iodide (880 mg; 587 mmol) in acetone (10 mL) and the reaction mixture stirred in the dark for 18 hours. The resulting slurry was filtered, the bicyclic acetal (2.00 g; 4.60 mmol) was added and the resulting solution was heated at 50° C. for 8 hours. The solvent was switched into cyclohexane (10 mL) and the product was removed by filtration to afford the quaternary salt as a pale yellow solid (2.76 g; 89%): mp 169–171° C.; $[\alpha]^{25}_{589}$ =−0.86° (c=2.05, MeOH); $^1$H NMR; IR (KBr)3278,3059, 1098, 959 cm$^{-1}$.

EXAMPLE 9

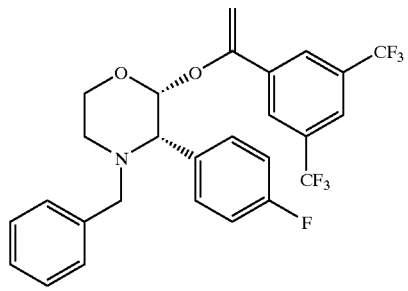

(2R-cis)-2-[[1-[3.5-bis(trifluoromethyl)phenyl] ethenyl]oxy]-3-(4-fluorophenyl)-4-(phenylmethyl) mopholine A slurry of quaternary salt 19 (2.00 g; 2.98 mmol) in ethanol (3 mL) was heated at 40° C. Sodium hydroxide (2N, 1.64 mL; 3.28 mmol) was added and heating was continued until dissolution occurred. After 20 minutes the reaction was seeded with (2R-cis)-2-[[1-[3.5-bis(trifluoromethyl) phenyl]-ethenyl]oxy]-3-(4-fluorophenyl)4-(phenylmethyl) mopholine (20 mg). After 40 minutes at 40° C. much precipitation of (2R-cis)-2-[[1-[3.5-bis(trifluoromethyl) phenyl]-ethenyl]oxy]-3-(4-fluorophenyl)-4-(phenylmethyl) mopholine occurred. The reaction was heated at 75° C. for a further 4 hours and then allowed to cool. An ethanol/water mixture (4:3, 7 mL) was added over 45 minutes. After 1 hour the product was isolated by filtration and washed twice with 1:1 ethanol-water. After drying 1.46 g (2R-cis)-2-[[1-[3.5-bis(trifluoromethyl)phenyl]-ethenyl]oxy]-3-(4-fluorophenyl)-4-(phenylmethyl)-mopholine was obtained as a white powder (90%). SFC analysis (OD column, 3% MeOH isocratic) indicated >>99% ee of the desired enantiomer: mp 101–103° C.; $[\alpha]^{25}_{589}$ =114.1°(c=1.18, MeOH); $^1$H NMR ; IR (KBr) 3028, 2882, 1466, 753 cm$^{-1}$. Anal. Calcd for C$_{27}$H$_{22}$F$_7$NO$_2$: C 61.72; H, 4.22; F, 25.31; N 2.67. Found: C, 61.22; H, 4.13; F, 25.09; N, 2.61.

EXAMPLE 10

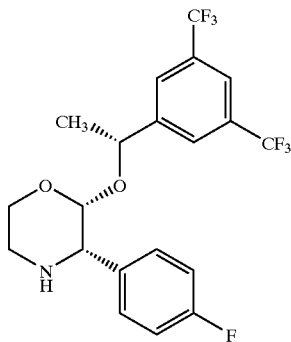

(2R, 2-alpha-R, 3a)-2-[1-[3,5-bis(trifluoromethyl) phenyl]ethoxy-3-(4-fluorophenyl)-1,4-oxazine A solution of (2R-cis)-2-[[1-[3.5-bis(trifluoromethyl) phenyl]-ethenyl]oxy]-3-(4-fluorophenyl)-4-(phenylmethyl) mopholine (1082 g, 94% pure, 1.94 moles) in 1:1 ethyl acetate:ethanol (13 L) was mixed with 10% palladium-on-carbon (165 g). The resulting slurry was treated with hydrogen (40 psi, 20–25° C.) for 12 hours. The reaction was monitored by hydrogen uptake and HPLC. The vessel was vented, and the catalyst was removed by filtration. After washing the catalyst with 1:1 ethyl acetate:ethanol (6 L) followed by ethyl acetate (2 L), the combined organic phases containing crude product were vacuum concentrated. A second batch, starting with 1078 g of (2R-cis)-2-[[1-[3,5-bis(trifluoromethyl)phenyl]ethenyl]oxy]-3-(4-fluorophenyl)-4-(phenylmethyl)mopholine (1.93 moles) was prepared. The resulting crude product was vacuum concentrated and combined with the first batch. The combined batches of crude product were flushed with methyl-t-butyl ether (2×3 L) in order to remove residual ethyl acetate and ethanol, then were dissolved in methyl-t-butyl ether (3 L). The solution was assayed to contain 1348 g (3.09 moles, 80% yield) of the title compound (as the free base). Alternatively, 60 g of the vinyl ether, 650 mL of methyl t-butyl ether (MTBE), and 18 g of 5% Pd on alumina were stirred under 40 psi hydrogen pressure at 40° for 12 H. Assay yield was 87%, with a 91:9 ratio of diastereomers. At the end of the reaction age, the catalyst was removed by filtration through Solka-Floc, then the filtrate was concentrated to 140 mL.

The first batch was treated with a warm (40° C.) solution of p-toluene sulfonic acid monohydrate (575 g, 3.03 moles) in methyl-t-butyl ether (3.2 L). The p-toluene sulfonic acid salt began to crystallize during the addition. The batch was cooled to ambient temperature and hexane (24 L) was added. The batch was aged for 2 hours, then the product was collected by filtration. The solid was washed with 4:1 hexane:methyl-t-butyl ether (2×2.5 L), then dried under nitrogen (1761 g (1655 g corrected for purity) of [2R-[2a (R*),3a]]-2-[1-[3,5-bis(trifluoromphenyl]-5 ethoxy]-3-(4-fluorophenyl)morpholine 4-methylbenzenesulfonate (salt), 94 wt. % pure, 70% yield). Alternatively, to the second solution was added a solution of 16.0 g p-TsOH monohydrate in 64 mL MTBE at 35° over a 20 min period. The tosylate salt crystallized as a thick slurry. Then 520 mL of hexanes was added over 1 h, and the slurry was stirred 2 h at ambient temperature. The slurry was filtered, washed with 2×60 mL 1:4 MTBE: hexanes, and dried by air suction to give 51.9 g of the tosylate salt (75% yield) containing 0.9% of the undesired diastereomer.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

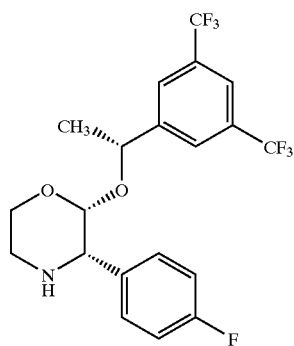

which comprises:

(1) contacting a compound of the formula:

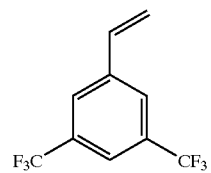

with an oxidizing agent which is osmium tetroxide/N-methyl morpholine to give a compound of the formula:

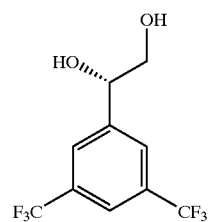

(2) activating the compound from step 1 with an activating agent which is methanesulfonyl chloride and contacting the activated compound with ethanolamine to give a compound of the formula:

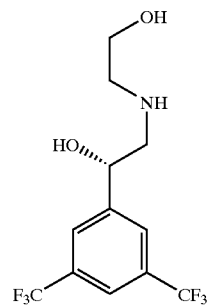

(3) condensing the compound from step 2 with glyoxal and 4-fluoroboronic acid to give a compound of the formula:

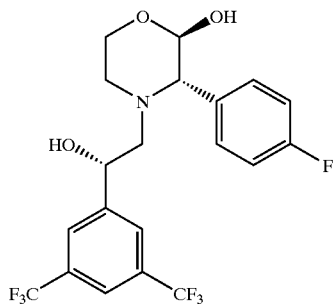

(4) intramolecular coupling of the compound from step 3 to give a compound of the formula:

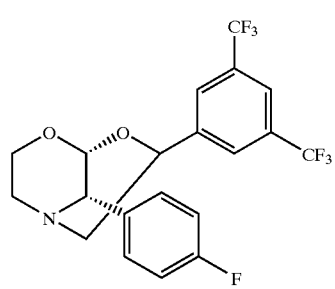

(5) quarternizing the amino group of the compound from step 4 to give a compound of the formula:

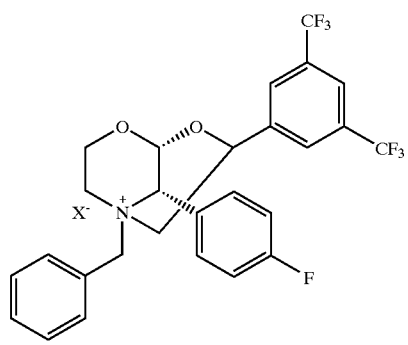

(wherein X⁻ is a counterion)

(6) hydrolysis of the compound from step 5 to give a compound of the formula:

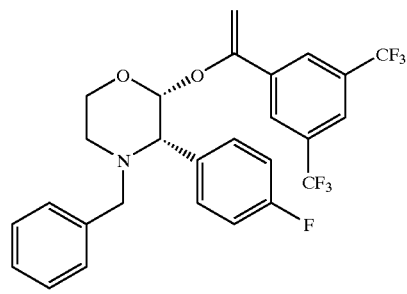

and (7) hydrogenation of the compound from step 6 to give the compound of the formula:

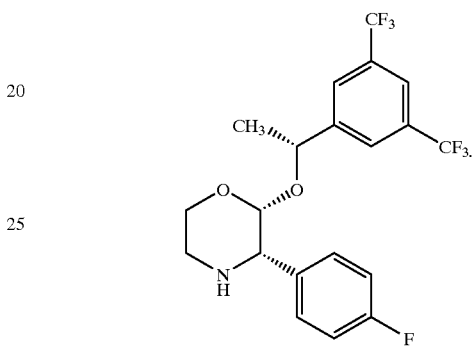

2. The process of claim 1 wherein Step (4) the intramolecular coupling of the activated compound is conducted under Mitsunobu conditions.

3. The process of claim 1 wherein Step (5) the amino group of the compound is quarternized with a benzyl halide.

4. The process of claim 1 wherein Step (6) the hydrolysis is conducted with an inorganic base.

5. The process of claim 1 wherein Step (7) the hydrogenation is conducted under conditions of catalytic hydrogenation.

6. The process of claim 1 wherein Step (7) the catalytic hydrogenation is conducted with a palladium catalyst.

7. The process of claim 6 wherein the hydrogenation catalyst is selected from: palladium on carbon, palladium on alumina, palladium on barium sulfate, palladium on calcium carbonate, palladium on barium carbonate, palladium on strontium carbonate, palladium on silica, and palladium hydroxide on carbon.

8. The process of claim 7 wherein the hydrogenation catalyst is palladium on carbon.

* * * * *